US009649424B2

(12) United States Patent
Sato et al.

(10) Patent No.: US 9,649,424 B2
(45) Date of Patent: May 16, 2017

(54) BLOOD COMPONENT SEPARATION SYSTEM AND SEPARATION MATERIAL

(75) Inventors: Nobuhiko Sato, Osaka (JP); Shinya Yoshida, Osaka (JP); Akira Kobayashi, Osaka (JP); Masaru Nakatani, Osaka (JP)

(73) Assignee: KANEKA CORPORATION, Osaka-shi, Osaka (JP)

( * ) Notice: Subject to any disclaimer, the term of this patent is extended or adjusted under 35 U.S.C. 154(b) by 622 days.

(21) Appl. No.: 13/381,433

(22) PCT Filed: Jun. 28, 2010

(86) PCT No.: PCT/JP2010/060975
§ 371 (c)(1),
(2), (4) Date: Feb. 24, 2012

(87) PCT Pub. No.: WO2011/001936
PCT Pub. Date: Jan. 6, 2011

(65) Prior Publication Data
US 2012/0141975 A1    Jun. 7, 2012

(30) Foreign Application Priority Data

Jun. 30, 2009    (JP) ................................. 2009-156383

(51) Int. Cl.
| | | |
|---|---|---|
| *C12N 15/10* | (2006.01) | |
| *A61M 1/36* | (2006.01) | |
| *A61M 1/02* | (2006.01) | |
| *B01D 39/16* | (2006.01) | |
| *D04H 1/4382* | (2012.01) | |

(52) U.S. Cl.
CPC ............ *A61M 1/3679* (2013.01); *A61M 1/02* (2013.01); *A61M 1/0209* (2013.01); *B01D 39/1623* (2013.01); *D04H 1/4382* (2013.01); *A61M 2202/0427* (2013.01); *A61M 2202/0429* (2013.01); *A61M 2202/0439* (2013.01); *B01D 2239/1208* (2013.01); *B01D 2239/1233* (2013.01); *C12N 15/1017* (2013.01)

(58) Field of Classification Search
CPC ............ A61K 2300/00; A61K 38/1754; A61K 38/1825; A61K 38/1841; A61K 38/1858; A61K 35/14; A61K 35/12; A61K 35/36; A61K 36/185; A61K 36/22; A61K 36/28; A61K 36/45; A61K 36/53; A61K 9/0014; A61K 2039/505; A61K 31/711; A61K 35/03
USPC ............................................. 435/0.12, 2, 325
See application file for complete search history.

(56) References Cited

U.S. PATENT DOCUMENTS

| 5,164,087 A | 11/1992 | Naoi et al. |
|---|---|---|
| 5,543,062 A * | 8/1996 | Nishimura .................... 210/782 |
| 2005/0061962 A1 | 3/2005 | Mueth et al. |
| 2005/0130301 A1 * | 6/2005 | McKay et al. ................. 435/372 |
| 2006/0180542 A1 | 8/2006 | Mari et al. |
| 2008/0021365 A1 | 1/2008 | Kobayahi et al. |
| 2009/0142835 A1 | 6/2009 | Kobayashi et al. |
| 2012/0141975 A1 | 6/2012 | Sato et al. |

FOREIGN PATENT DOCUMENTS

| EP | 0331174 | 9/1989 |
|---|---|---|
| EP | 1167518 | 1/2002 |
| EP | 1947170 | 7/2008 |
| JP | 1-224325 | 9/1989 |
| JP | 06-246156 | 9/1994 |
| JP | 08-104643 | 4/1996 |
| JP | 2001-078757 | 3/2001 |
| JP | 2001-518792 | 10/2001 |
| JP | 2004-121144 | 4/2004 |
| JP | 2004-129550 | 4/2004 |
| JP | 2005-224787 | 8/2005 |
| JP | 2007-289076 | 11/2007 |
| JP | 2008-022822 | 2/2008 |
| WO | 98/32840 | 7/1998 |
| WO | 2006071496 | 7/2006 |

OTHER PUBLICATIONS

International Search Report for International Application No. PCT/JP2010/060975 mailed on Oct. 26, 2010.
Yasutake, Mikimoto, et al., "SCID—repopulating activity of human umbilical cord blood-derived hematopoietic stem and/or progenitor cells in a nonobese diabetic/Shi-SCID mice serial xenotransplantation model and immune cell activities in vitro: a comparative study of the filter method and the hydroxyethyl starch method", Transplantation and Cellular Engineering, vol. 45, Dec. 2005, Transfusion.
International Preliminary Report on Patentability for International Application No. PCT/JP2010/060975 mailed on Feb. 14, 2012.
Wang Dawei, A Study on the Nonwoven Filter Used for Removing White Cells; Heilongjiang Textile, p. 19-21 (2000).
Chinese Office Action for Chinese Application No. 201080029525.8 mailed on Apr. 23, 2013.
International Search Report for Singapore Application No. 201109701-1 issued on Nov. 27, 2013.

(Continued)

*Primary Examiner* — Scott Long
*Assistant Examiner* — Nghi Nguyen
(74) *Attorney, Agent, or Firm* — Amin, Turocy & Watson LLP (57) ABSTRACT

The present invention relates to a separation system and a separation material for easily and rapidly separating a red blood cell-rich fraction, a white blood cell-rich fraction, and/or a platelet-rich fraction from a biological fluid containing these blood cell components without the necessity of performing centrifugation. The separation of a red blood cell-rich fraction, a white blood cell-rich fraction, and/or a platelet-rich fraction from a biological fluid can be accomplished by capturing white blood cells and platelets on a blood cell separation material by contacting the biological fluid with the blood cell separation material, thereby providing a red blood cell-rich fraction; and recovering a white blood cell-rich fraction by separating white blood cells captured from the resulting blood cell separation material using a separation solution.

15 Claims, 2 Drawing Sheets

(56) References Cited

OTHER PUBLICATIONS

Ke Qinfei. "Study on the Leukocyte Filtration Model of Nonwoven Filter", Journal of China Textile University, College of Textile, China Textile University, vol. 26, No. 2, Apr. 2000, Shanghai.
Ke Qinfei and He Fumin. "A Study on the Nonwoven Filter Used for Removing White Cells", Journal of China Textile University, College of Textile, China Textile University, vol. 25, No. 2, pp. 73-75, Apr. 1999, Shanghai.
Binran. "Handbook of Chemistry", Applied Chemistry, 6th Edition, Maruzen Co., Ltd., Jan. 30, 2003, pp. 827-828.
Koza. "Encyclopedia of Experimental Chemistry", 27, 4th Edition, Seibutsu yuki (Bioorganic), May 5, 1991, pp. 142-146.
M. Yasutake, et al. "Stem cell collection filter system for human placental/umbilical cord blood processing", Vox Sanguinis, 2001, vol. 80, pp. 101-105.
S. O. Sowemimo-Coker, et al. "A simple filtration system for red blood cell depletion and volume reduction in routine processing of human umbilical cord blood", Vox Sanguinis, 2009, vol. 96, pp. 138-145.

\* cited by examiner

BLOOD COMPONENT SEPARATION SYSTEM AND SEPARATION MATERIAL

TECHNICAL FIELD

The present invention relates to a method for separating a red blood cell-rich fraction, a white blood cell-rich fraction, and/or a platelet rich-fraction from a biological fluid containing these blood cell components. The present invention also relates to a separation material and a separation method that can selectively recover, in particular, a mononuclear cell-rich fraction containing a hematopoietic stem cell among white blood cells.

BACKGROUND ART

Recent rapid developments in hematology and scientific technology have allowed wide spread of a treatment style that enhances therapeutic effects and reduces side effects in which only a blood fraction necessary for the treatment is separated from a biological fluid such as whole blood, bone marrow, umbilical cord blood, or a tissue extract and administered to a patient without administering unnecessary fractions.

One example thereof is blood transfusion. Red blood cell products are blood products used to treat lack of oxygen caused by hemorrhage, lack of red blood cells, or hypofunction of red blood cells. Because white blood cells may induce an abnormal immunoreaction and a side effect such as graft versus host disease (GVHD), the white blood cells are unnecessary for these products and should be removed using a filter. In some cases, not only white blood cells but also platelets are removed.

Platelet products are blood products used to treat patients with hemorrhage or hemorrhagic tendencies due to lack of a blood coagulation factor. For these products, unnecessary cells and components other than platelets are removed by centrifugation and only desired platelet components are recovered.

Also, hematopoietic stem cell transplants have recently become popular as treatment for leukemia or solid cancers. In the transplants, cells required for the treatment (white blood cells, in particular mononuclear cells) have been separated and administered. In addition to bone marrow and peripheral blood, umbilical cord blood has attracted attention as a source of the hematopoietic stem cells because of its advantages such as small burden on donors and high proliferative ability. Recent studies have suggested that menstrual blood is also rich in stem cells, and this suggestion indicates the possibility of using menstrual blood, which has conventionally been discarded, as a valuable source of stem cells.

In the case of bone marrow or peripheral blood, white blood cells (in particular mononuclear cells) should be separated and purified by removing unnecessary cells and administered. Also in the case of umbilical cord blood, since umbilical cord blood banking for blood relatives has become popular and umbilical cord blood then needs to be cryopreserved until used, white blood cells are separated and purified in order to prevent red blood cell hemolysis that may occur during cryopreservation.

Centrifugation using a specific gravity solution containing ficoll and centrifugation using hydroxyethyl starch as a red blood cell sedimentation agent have been proposed as separation methods, but have a problem of contamination of bacteria and other foreign matter because these processes cannot be carried out in closed systems. Recent documents have also reported cell separation methods in which white blood cells are recovered using a filter material that captures only white blood cells and does not capture red blood cells and platelets, without performing centrifugation (Patent Documents 1 and 2). However, red blood cells and platelets cannot be separated from each other by these methods.

Currently, different separation methods appropriate to respective target components have been used, specifically: separation filters are used for red blood cell products; centrifugation is used for platelet products; and centrifugation using a specific gravity solution or a red blood cell sedimentation agent is used for white blood cell products. Although red blood cells, platelets, and white blood cells can all be theoretically recovered from a single source sample of blood, bone marrow, umbilical cord blood, or the like, the conventional separation methods let useful cells go to waste. This has created a demand for separation techniques that enable red blood cells, white blood cells, and platelets in a single source sample to be separated rapidly without performing complicated operations.

There has been another demand for further improving, in particular, the purity of a mononuclear cell fraction containing hematopoietic stem cells among white blood cells. However, the current techniques still allow high contamination of granular leukocytes, which has created a need to reduce the granular leukocyte contamination to lower levels than the current levels (Non-Patent Document 1).

It has also been suggested that the use of a highly viscous solution containing dextran as a solution for recovering white blood cells or mononuclear cells captured on a filter increases the recovery rates of white blood cells and mononuclear cells (Patent Document 2). This method, however, has a problem that such a dextran solution is so viscous that it is difficult to push it out of a syringe by hand, which in turn has created a demand for separation solutions that enable easy recovering using a syringe and also enable white blood cells or mononuclear cells to be recovered at a high recovery rate.

Patent Document 1: JP 2001-518792 T
Patent Document 2: WO 98/32840
Non-Patent Document 1: TRANSFUSION, Vol. 45, pp. 1899-1908, 2005

SUMMARY OF THE INVENTION

An object of the present invention is to provide a method that can rapidly and easily separate a red blood cell-rich fraction, a white blood cell-rich fraction, and/or a platelet-rich fraction from a biological fluid containing these blood cell components without requiring centrifugation. A further object of the present invention is to provide a separation material and a separation method that can recover, in particular, a mononuclear cell-rich fraction with low contamination of granular leukocytes, among white blood cells.

The present inventors have intensively studied to achieve a method that enables blood cell components to be separated from a biological fluid without requiring centrifugation, which has been difficult to achieve, and have found that a red blood cell-rich fraction, a white blood cell-rich fraction, and/or a platelet-rich fraction can be separated from a biological fluid as follows: the red blood cell-rich fraction is obtained by, capturing white blood cells and platelet on a blood cell separation material of a specific type; and then the white blood cell-rich fraction is obtained by recovering the white blood cells captured on the blood cell separation material using a separation solution. Thus, the present inventors have completed the present invention.

The present invention relates to a method that can separate a red blood cell-rich fraction, a white blood cell-rich fraction, and/or a platelet-rich fraction from a biological fluid containing these blood cell components, by using a blood cell separation material that is able to capture white blood cells and platelets and allows separation and recovery of a white blood cell-rich fraction. Accordingly, the method of the present invention is completely different from the conventional white blood cell capture and recovery methods in which a white blood cell removal filter is used or a material that substantially allows platelets to pass therethrough is used as disclosed in Patent Documents 1 and 2.

The present inventors have also found that in particular a mononuclear cell-rich fraction which contains a high level of mononuclear cells among white blood cells can be efficiently separated by using a nonwoven fabric that has a specific density and a specific fiber diameter, as a blood cell separation material.

Specifically, the present invention relates to a method for separating blood cell components from a biological fluid, which includes:

(a) capturing white blood cells and platelets on a blood cell separation material by contacting the biological fluid with the blood cell separation material, thereby providing a red blood cell-rich fraction; and (b) separating a white blood cell-rich fraction from the resulting blood cell separation material using a separation solution.

Preferably, the blood cell separation material is packed in a container having an inlet and an outlet for the biological fluid, and the contact of the biological fluid with the blood cell separation material is accomplished by introducing the biological fluid from the inlet.

Preferably, in the step (a), after the contact of the biological fluid with the blood cell separation material, remaining red blood cells are washed out of the resulting blood cell separation material with a washing solution.

Preferably, in the step (b), the separation solution is introduced from the outlet for the biological fluid to separate and recover white blood cells.

Preferably, the separation solution includes physiological saline, a buffer, dextran, a culture medium, or an infusion.

Preferably, the biological fluid is blood, bone marrow, umbilical cord blood, menstrual blood, or a tissue extract.

Preferably, before the contact of the blood cell separation material with the biological fluid in the step (a), the blood cell separation material is preliminarily contacted with a solution.

Preferably, the solution for preliminarily contacting the blood cell separation material includes physiological saline or a buffer.

Preferably, the blood cell separation material includes a nonwoven fabric. Preferably, the nonwoven fabric includes a split fiber.

Preferably, the nonwoven fabric includes a polyester fiber, a polypropylene fiber, a nylon fiber, or an acrylic fiber. Preferably, the polyester fiber is a polyethylene terephthalate fiber or a polybutylene terephthalate fiber. Preferably, the nonwoven fabric includes a nylon fiber, a polypropylene fiber, or a polybutylene terephthalate fiber.

Preferably, the nonwoven fabric has a density K of $2.0 \times 10^4$ to $1.9 \times 10^5$ and has a fiber diameter of 1 μm to 15 μm, and the white blood cell-rich fraction is a mononuclear cell-rich fraction.

Preferably, the separation solution is a solution having a viscosity of from 1 mPa·s or higher to lower than 5 mPa·s.

Preferably, a platelet recovery rate of the white blood cell-rich fraction or the mononuclear cell-rich fraction is not more than a white blood cell recovery rate of the white blood cell-rich fraction or the mononuclear cell-rich fraction. Preferably, a platelet recovery rate of the white blood cell-rich fraction or the mononuclear cell-rich fraction is not more than a mononuclear cell recovery rate of the white blood cell-rich fraction or the mononuclear cell-rich fraction.

Preferably, a ratio of a mononuclear cell recovery rate to a granular leukocyte recovery rate of the white blood cell-rich fraction or the mononuclear cell-rich fraction is larger than 1.0.

Preferably, the white blood cell-rich fraction or the mononuclear cell-rich fraction includes a hematopoietic stem cell, a mesenchymal stem cell, or a CD34-positive cell.

The present invention also relates to a red blood cell-rich fraction, a white blood cell-rich fraction, or a platelet-rich fraction separated by the above-described method.

The present invention further relates to a blood cell separation material which includes a nonwoven fabric that allows separation of a mononuclear cell-rich fraction from a biological fluid, wherein the nonwoven fabric has a density K of $2.0 \times 10^4$ to $1.9 \times 10^5$ and has a fiber diameter of 1 μm to 15 μm.

Preferably, the blood cell separation material includes a nylon fiber, a polypropylene fiber, or a polybutylene terephthalate fiber.

The present invention further relates to a blood cell separation device including the above-described blood cell separation material, wherein a laminate of layers of the blood cell separation material is packed in a container having an inlet and an outlet for a biological fluid.

The present invention further relates to a blood cell separation device which includes:

the container packed with a laminate of layers of the blood cell separation material;

a flow-path opening and closing means located upstream of the inlet of the container;

a white blood cell-rich fraction recovery means connected to the flow-path opening and closing means; and a separation solution introducing means located downstream of the outlet of the container.

The present invention further relates to a separation solution for recovering white blood cells captured on a blood cell separation material or a nonwoven fabric, which has a viscosity of from 1 mPa·s or higher to lower than 5 mPa·s. Preferably, the separation solution is free from dextran.

The method of the present invention can easily and rapidly separate a red blood cell-rich fraction, a white blood cell-rich fraction, and/or a platelet-rich fraction from a biological fluid such as whole blood, bone marrow, umbilical cord blood, menstrual blood, or a tissue extract. The method of the present invention enables red blood cells, platelets, and white blood cells in a biological fluid to be separated and recovered although the conventional methods cannot separate and recover all these components, and cannot recover some of these. In addition, the use of the nonwoven fabric in the present invention as a blood cell separation material provides a mononuclear cell-rich fraction.

The method of the present invention provides a red blood cell-rich fraction with remarkably low contamination of other blood cells. Such a fraction can be used for blood transfusion without being subjected to any processes. The method of the present invention provides a white blood cell-rich fraction or a mononuclear cell-rich fraction with remarkably low contamination of red blood cells. Such a fraction will hardly receive bad influence caused by red blood cell hemolysis or the like even if it is cryopreserved until used. A filter constituted by a container packed with the separation material of the present invention can be used in an aseptic closed system, which means that fractions can be aseptically recovered and used to amplify cells therein, without being subjected to any processes.

The blood cell separation material of the present invention can be used as a filter for the preparation of therapeutic cells for regenerative medicine, such as leukemia treatment, cardiac muscle regeneration, and blood vessel regeneration. The blood cell separation material of the present invention is also very useful as a filter for the preparation of cell sources for regenerative medicine as well as for the preparation of blood transfusion products because the use of the blood cell separation material provides a white blood cell-rich fraction or a mononuclear cell-rich fraction that is rich in hematopoietic stem cells. Thus, the blood cell separation material makes it possible to prepare highly safe therapeutic cells that have fewer side effects.

BEST MODE FOR CARRYING OUT THE INVENTION

The following discussion provides a detailed description of the present invention and is not intended to limit the scope of the present invention.

1. Method for Separating Blood Cell Components From a Biological Fluid

The method for separating blood cell components from a biological fluid according to the present invention includes:

(a) capturing white blood cells and platelets on a blood cell separation material by contacting the biological fluid with the blood cell separation material, thereby providing a red blood cell-rich fraction; and (b) separating a white blood cell-rich fraction from the resulting blood cell separation material using a separation solution.

In the method of the present invention, the blood cell separation material may be used without using any container or may be packed in a container having an inlet and an outlet for a biological fluid. For practical reasons, the latter manner in which the separation material is packed in a container is preferred. The blood cell separation material may be used either in the form of a flat sheet cut to an appropriate size or in a rolled-up form to treat the biological fluid. In the case that the blood cell separation material is packed in a container having an inlet and an outlet for a biological fluid, the biological fluid is introduced from the inlet so as to contact the blood cell separation material.

(a) Biological Fluid Feeding Process

In this process, the biological fluid is introduced from the inlet of the container packed with the blood cell separation material. As a result, white blood cells and platelets are captured, and thereby a red blood cell-rich fraction is obtained.

The term "biological fluid" is intended to include whole blood, bone marrow, umbilical cord blood, menstrual blood, and tissue extracts and to further include fluids obtained by rough separation of these. The animal origin thereof is not limited and is any species of mammals such as humans, bovines, mice, rats, swine, monkeys, dogs, and cats. The biological fluid may be derived from any of umbilical cord blood, bone marrow, and tissues, in addition to blood of these animals. Also, the type of anticoagulants for the biological fluid is not limited, and any of citrate anticoagulants (e.g. ACD (acid-citrate-dextrose) solution, CPD (citrate-phosphate-dextrose) solution, CPDA (citrate-phosphate-dextrose-adenine) solution), heparin, low-molecular-weight heparin, Futhan (nafamostat mesilate), and EDTA may be used for anticoagulation of the biological fluid. Further, the storage conditions of the biological fluid are not limited at all as long as the conditions cause no influence on the intended uses of the fractions.

In order to introduce the biological fluid from the biological fluid inlet of the container packed with the blood cell separation material, the biological fluid may be fed from a container containing the biological fluid through a fluid feed line either by free fall under gravity or by a pump. Alternatively, a syringe containing the biological fluid may be directly connected to the container and then pressed by hand. In the case that the biological fluid is fed by a pump, too high a feed rate may lead to low separation efficiencies, and too low a feed rate may elongate the process time. Based on these considerations, the feed rate may be, but is not limited to, 0.1 mL/min to 100 mL/min.

A process for immersion of the separation material into physiological saline or a buffer may be performed as a pretreatment prior to the biological fluid feeding process. This procedure may not be necessary but may be optionally performed in some cases because the immersion of the separation material into such a solution is expected to contribute to increasing the separation efficiencies and securing blood flow-paths. The pretreatment solution does not need to be the same as that used in the washing process described later but may be the same for simplicity of the line system and handleability because the same solution bag can be shared. For practical reasons, the volume of the pretreatment solution is preferably about 1 to 100 times the volume of the capacity of the container to be packed with the blood cell separation material.

After white blood cells and platelets are captured on the blood cell separation material, the resulting blood cell separation material is washed. In this procedure, a washing solution is passed through the container in the same direction, so that red blood cells remaining in the container are effectively recovered and separated. Since the washing solution mainly recovers only red blood cells, the recovered solution may be mixed with a fluid that has passed through the container after the introduction of the biological fluid, and the mixture may be used as a red blood cell-rich fraction.

In order to allow passage of the washing solution in the same direction as that of the biological fluid feeding from the washing solution inlet, the washing solution may be fed through a line either by free fall under gravity or by a pump. In the case that the biological fluid is fed by a pump, the flow rate is similar to that of the biological fluid feeding, and may be specifically, but is not limited to, 0.1 mL/min to 100 mL/min. The volume of the washing solution depends on the capacity of the container. Too little washing solution may leave more red blood cell components in the container, and too much washing solution may lead to low separation efficiencies and remarkably elongate the process time. Based on these considerations, the volume of the washing solution is preferably set to about 0.5 to 100 times the volume of the capacity of the container.

Any washing solution can be used as long as it is able to wash out only red blood cells, reduce the contamination of other blood cells in a white blood cell-rich fraction, and maintain blood cells captured on the blood cell separation material. Preferred are common buffers such as physiological saline, Ringer's solution, media for cell culture, and phosphate buffer.

(b) White Blood Cell-Rich Fraction Separation Process

The separation solution is introduced to the container packed with the blood cell separation material from the direction opposite to the biological fluid feeding direction (from the biological fluid outlet), so that a white blood cell-rich fraction is obtained. The reason why the separation solution is introduced from the direction opposite to the biological fluid feeding direction is that the white blood cell recovery rate of the white blood cell-rich fraction can be increased by introducing the separation solution from the outlet. The introduction of the separation solution can be accomplished by pouring the separation solution into a syringe or the like, and then strongly pressing a plunger of the syringe by hand or by using an instrument. The volume and flow rate of the recovery solution depend on the capacity of the container and the amount of the sample. The volume is preferably, but is not limited to, about 1 to 100 times the volume of the capacity of the container. The flow rate is preferably, but is not limited to, 0.5 mL/sec to 20 mL/sec.

The separation solution is not particularly limited, as long as it is a hypotonic solution. Examples thereof include solutions that have been used for injection (e.g. physiological saline, Ringer's solution), buffers, media for cell culture, and infusions.

In order to enhance the recovery rate of captured cells, the viscosity of the recovery solution may be increased. For this purpose, to the separation solution may be added a substance such as, but not limited to, albumin, fibrinogen, globulin, dextran, hydroxyethyl starch, hydroxyethyl cellulose, collagen, hyaluronic acid, and gelatin. However, if the recovery solution contains a high level (approximately not less than 10%) of dextran or the like, the viscosity thereof is 5 mPa·s or higher, and therefore it is likely to be difficult to perform the recovery by operating a syringe by hand. Based on this consideration, the separation solution is preferably free from dextran or preferably has a dextran concentration controlled such that the viscosity is in the range from 1 mPa·s or higher to lower than 5 mPa·s.

2. Blood Cell Components

The red blood cell-rich fraction refers to a flow-through fraction that has a red blood cell recovery rate more than its other blood cell component recovery rate (white blood cell recovery rate, platelet recovery rate). The red blood cell recovery rate of the red blood cell-rich fraction is not less than 80%, preferably not less than 90%, and more preferably not less than 95%. Here, the red blood cell recovery rate is a percentage determined by dividing the total number of red blood cells in the red blood cell-rich fraction by the total number of red blood cells before the above-described processes.

Regarding the white blood cell content of the red blood cell-rich fraction, the white blood cell recovery rate that is a percentage determined by dividing the total number of white blood cells in the red blood cell-rich fraction by the total number of white blood cells before the above-described processes, is not more than 10%, and preferably not more than 5%. Regarding the platelet content of the red blood cell-rich fraction, the platelet recovery rate that is a percentage determined by dividing the total number of platelets in the red blood cell-rich fraction by the total number of platelets before the above-described processes, is less than 60%, preferably not more than 40%, and more preferably not more than 20%.

The white blood cell-rich fraction, which is separated and recovered by the method of the present invention using the blood cell separation material in the present invention, refers to a recovered separation solution that is characterized in that any one of its white blood cell recovery rate, mononuclear cell recovery rate, and granular leukocyte recovery rate is not less than half of its other blood cell component recovery rate (red blood cell recovery rate, platelet recovery rate). A fraction having a lymphocyte recovery rate of not less than half of its other blood cell component recovery rate (red blood cell recovery rate, platelet recovery rate) is also included in the white blood cell-rich fraction herein. The white blood cell recovery rate is not less than 45%, preferably not less than 60%, and more preferably not less than 80%. Here, the white blood cell recovery rate is a percentage determined by dividing the total number of white blood cells in the white blood cell-rich fraction by the total number of white blood cells before the above-described processes. The mononuclear cell recovery rate and granular leukocyte recovery rate can also be determined in the same manner from the total numbers thereof, or alternatively may be each determined by multiplying a positive ratio determined using a flow cytometer or the like by the number of white blood cells.

The white blood cell-rich fraction or the mononuclear cell-rich fraction preferably has a platelet recovery rate of not more than its white blood cell recovery rate. The white blood cell-rich fraction or the mononuclear cell-rich fraction preferably has a platelet recovery rate of not, more than its mononuclear cell recovery rate. The white blood cell-rich fraction or the mononuclear cell-rich fraction preferably includes a hematopoietic stem cell, a mesenchymal stem cell, or a CD34-positive cell.

Regarding the red blood cell content of the white blood cell-rich fraction, the red blood cell recovery rate that is a percentage determined by dividing the total number of red blood cells in the white blood cell-rich fraction by the total number of red blood,cells before the above-described processes, is not more than 10%, and preferably not more than 5%. Regarding the platelet content of the white blood cell-rich fraction, the platelet recovery rate that is a percentage determined by dividing the total number of platelets in the white blood cell-rich fraction by the total number of platelets before the above-described processes, is not more than 50%, preferably not more than 25%, more preferably not more than 10%, and further more preferably not more than 5%.

The platelet-rich fraction herein refers to a cell fraction which remains captured on the separation material after the white blood cell-rich fraction is recovered using the separation solution, and has a platelet recovery rate, which is a rate of recovery of platelets remaining captured on the separation material, of more than its other blood cell component recovery rate (red blood cell recovery rate, white blood cell recovery rate).

The white blood cell composition of the fraction separated and recovered using the separation solution can be controlled by using the nonwoven fabric disclosed herein, which has a density K of $2.0 \times 10^4$ to $1.9 \times 10^5$ and has a fiber diameter of 1 μm to 15 μm. The nonwoven fabric can be used, for example, for separation of mononuclear cells (lymphocytes+monocytes) and granular leukocytes to provide a mononuclear cell-rich composition (mononuclear cell-rich fraction). The mononuclear cell-rich fraction herein refers to a fraction separated and recovered using the separation solution which is characterized in that its mononuclear cell recovery rate is more than its granular leukocyte recovery rate or its other blood cell component recovery rate (red blood cell recovery rate, platelet recovery rate). Specifically, the ratio (mononuclear cell recovery rate)/(granular leukocyte recovery rate) is larger than 1.0, is preferably not less than 1.2, and more preferably not less than 1.5.

3. Blood Cell Separation Material

The material for the blood cell separation material is not particularly limited, and the following are mentioned as examples thereof based on considerations of sterilization resistance and safety of cells: synthetic polymers such as polyethylene terephthalate, polybutylene terephthalate, polyethylene, high-density polyethylene, low-density polyethylene, polyvinyl alcohol, vinylidene chloride, rayon, vinylon, polypropylene, acrylics (e.g. polymethyl methacrylate, polyhydroxyethyl methacrylate, polyacrylnitril, polyacrylic acid, polyacrylate), nylon, polyimide, aramids (e.g. aromatic polyamides), polyamide, cuprammonium rayon, carbons, phenolic resin, polyester, pulp, linen, polyurethane, polystyrene, and polycarbonate; natural polymers such as agarose, cellulose, cellulose acetate, chitosan, and chitin; inorganic materials such as glass; and metals. Among these, preferred are polyethylene terephthalate, polybutylene terephthalate, polypropylene, acrylics, nylon, polyurethane, and glass. One of these materials may be used alone, or any of these may be combined, mixed, or fused, if necessary. In addition, molecules having affinity for specific cells, such as proteins, peptides, amino acids, and saccharides, may be fixed thereto, if necessary.

The form of the blood cell separation material is not particularly limited and the blood cell separation material may be particles, a nonwoven fabric, a textile fabric, a sponge, a porous material, a mesh, or the like. In particular, the blood cell separation material preferably includes fibers, and more preferably includes a nonwoven fabric in terms of easy preparation and availability.

In the case that the form of the blood cell separation material is a nonwoven fabric, the nonwoven fabric preferably includes at least one of polyester fibers, polypropylene fibers, nylon fibers, and acrylic fibers. Preferred examples of polyester include polyethylene terephthalate and polybutylene terephthalate because they enhance the red blood cell separation efficiency and the white blood cell separation efficiency. The nonwoven fabric more preferably includes nylon, polypropylene, and/or polybutylene terephthalate in order to enhance the red blood cell separation efficiency and the white blood cell separation efficiency.

Methods for producing the nonwoven fabric are roughly classified into wet methods and dry methods, and specific examples thereof include, but are not limited to, resin bonding, thermobonding, spunlacing, needle punching, stitch bonding, spunbonding, and melt blowing. Since small fiber diameters lead to high blood cell separation efficiencies, melt blowing and spunlacing are preferred. Materials subjected to calendering or a plasma treatment may be used.

So-called split fibers, which are formed by splitting a multicomponent fiber into a plurality of fibers, are also suited as fibers for the nonwoven fabric because they have a complex structure of entangled fibers and enhance the blood cell separation efficiencies.

The density K (i.e. basis weight $(g/m^2)$/thickness (m)) of the separation material is preferably $1.0 \times 10^4$ to $5.0 \times 10^5$ from the viewpoint of efficiencies for separating the red blood cell-rich fraction, the white blood cell-rich fraction, and the platelet-rich fraction. In the case of recovery of the mononuclear cell-rich fraction, which is particular rich in mononuclear cells among white blood cells, the required density K is $2.0 \times 10^4$ to $1.9 \times 10^5$. The density K is more preferably $4.0 \times 10^4$ to $1.9 \times 10^5$ in terms of the mononuclear cell recovery rate, and more preferably $5.0 \times 10^4$ to $1.9 \times 10^5$ in order to reduce the granular leukocyte contamination to low levels.

The density K, which is defined as basis weight $(g/m^2)$/thickness (m), can be also represented by weight (g)/unit volume $(m^3)$. Namely, the density K may be determined by measuring the weight (g) per unit volume $(m^3)$ regardless of the form of the separation material. During the measurement, no pressure is applied to the separation material to avoid deformation. For example, a CCD laser displacement sensor (LK-035 produced by KEYENCE) or the like enables non-contact thickness measurement. It goes without saying that if a catalogue, manual or the like of a material to be used says the basis weight and the thickness of the material, the data may be used to determine the density K as basis weight $(g/m^2)$/thickness (m).

The fiber diameter of the separation material needs to be 1 μm to 15 μm. If the fiber diameter is less than 1 μm, the probability of clogging tends to be high. If the fiber diameter is more than 15 μm, white blood cells and/or platelets cannot be captured on the separation material, resulting in high levels of contamination of white blood cells and/or platelets in the red blood cell-rich fraction. This in turn leads to remarkably low efficiencies in separation of the white blood cell-rich fraction and the platelet-rich fraction. The fiber diameter is preferably 1 μm to 10 μm, more preferably 1 μm to 7 μm, and particularly preferably 1 μm to 5 μm in order to enhance the separation efficiencies.

The fiber diameter refers to the width of fiber in the perpendicular direction to the fiber axis, and can be determined by photographing the separation material made of a nonwoven fabric using a scanning electron microscope, measuring the diameters of fibers based on a scale on the photograph, and averaging the measured diameters. Namely, the fiber diameter herein means the average fiber diameter determined as described above, and is specifically the average of 50 or more fibers, and preferably the average of 100 or more fibers. It should be noted that when multiple fibers are overlapped, some fibers hinder measurement of the width of a target fiber, or some fibers which remarkably differ in diameter are present, the data of these fibers are not used to determine the fiber diameter.

In the case that the nonwoven fabric includes fibers of multiple types which largely differ in width, for example, differ in diameter by more than 7 μm, the fiber diameter is calculated for each fiber type. Since fibers with a smaller diameter have stronger influence on the separation efficiencies, the smaller fiber diameter is regarded as the fiber diameter of the nonwoven fabric. In the case of two types of fibers which differ in diameter by, for example, 7 μm or less, the both types are treated as the same type and the diameter thereof is determined.

In the separation method of the present invention, two or more separation materials as described above according to the present invention may be used together, or alternatively the separation material of the present invention and separation material (s) other than the separation material of the present invention may be used together. Namely, even a case in which a separation material having a fiber diameter of, for example, 15 to 30 μm is used is included in the scope of the separation method of the present invention, provided that at least one separation material made of any of the above-mentioned materials and having a density K and a fiber diameter within the above ranges is used together.

4. Blood Cell Separation Device

The blood cell separation device of the present invention is obtained by packing the blood cell separation material in a container having an inlet and an outlet for a biological fluid.

The blood cell separation device preferably further includes an inlet and an outlet for the washing solution, an inlet and an outlet for the separation solution, a red blood cell-rich fraction recovery means, a white blood cell-rich fraction recovery means (or a mononuclear cell-rich fraction recovery means), and the like for practical use. The recovery means may be bags. Further, the blood cell separation device preferably includes the container packed with a laminate of layers of the blood cell separation material; a flow-path opening and closing means located upstream of the inlet of the container; a white blood cell-rich fraction recovery means connected to the flow-path opening and closing means; and a separation solution introducing means located downstream of the outlet of the container.

Figure 3:
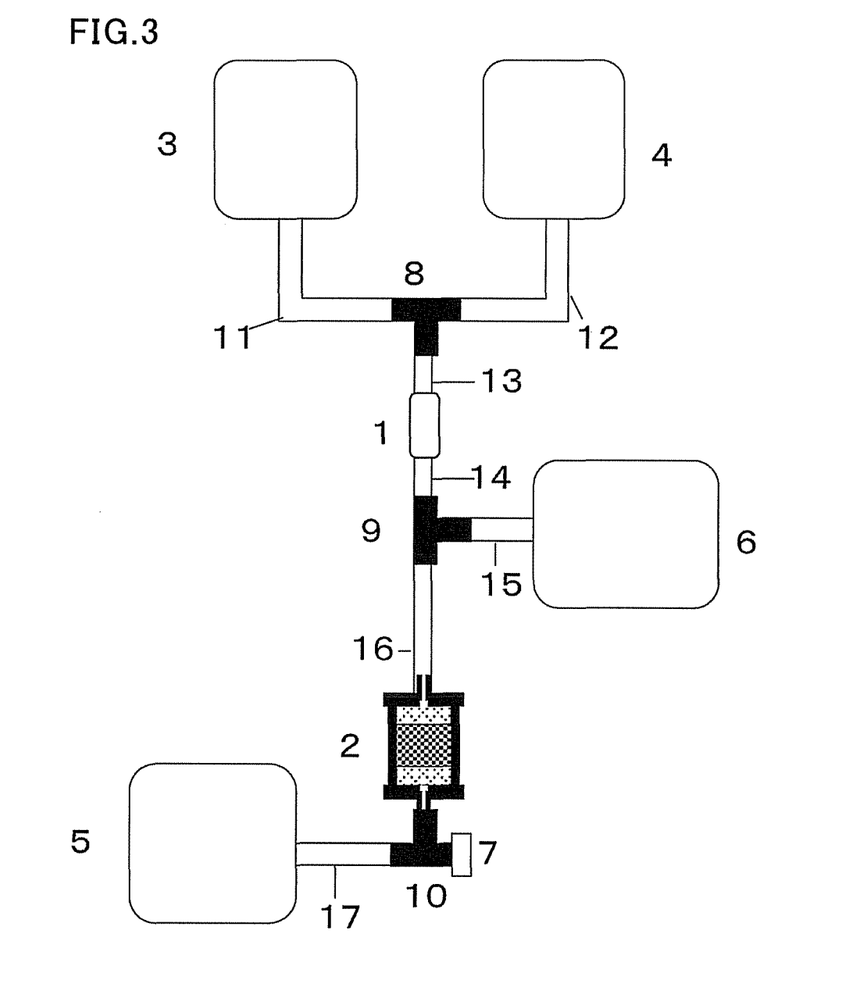
FIG. 3 is a view illustrating one example of a blood cell component separation system including the blood cell separation material of the present invention.

Specifically, the blood cell separation device, which has an inlet for introducing the biological fluid and an outlet for discharging the biological fluid, is preferably further characterized in that: the inlet for the biological fluid serves as an inlet for introducing the washing solution for washing out red blood cells remaining in the container, or the blood cell separation device has said washing solution inlet independently from the inlet for the biological fluid; the outlet for the biological fluid serves as an outlet for discharging the washing solution, or the blood cell separation device has said washing solution outlet independently from the outlet for the biological fluid; and the outlet for discharging the biological fluid and/or the washing solution serves as an inlet for introducing the separation solution, or the blood cell separation device has said separation solution inlet independently from the outlet for discharging the biological fluid and/or the washing solution. The inlet and outlet for the washing solution of the container may be the inlet and outlet for the biological fluid, respectively, and a line on the inlet side may be connected to both a blood bag and a washing solution bag via a flow-path opening and closing means such as a three-way stopcock. The outlet and inlet for the biological fluid may also serve as an inlet for introducing the separation solution and an outlet for recovering the separation solution, respectively, and a line may be similarly connected to bags, syringes, or the like via a three-way stopcock. FIG. 3 is a view illustrating one example of a blood cell separation system including the blood cell separation material of the present invention.

Preferably, a biological fluid storage bag, a separation solution recovery bag for recovering the white blood cell-rich fraction, a red blood cell-rich fraction recovery bag, and the like are also attached to the container. If these bags are connected to the inlet(s) and the outlet(s) for the solutions, the biological fluid can be separated in an aseptic closed system. Preferably, these bags after use can be cut off, and may have a shape like that of a commonly used blood bag or may have a flat plate shape of a cartridge type or the like. The white blood cell-rich fraction recovery bag or the mononuclear cell-rich fraction recovery bag may, for example, be a bag usable for cell culture or a cryopreservation resistant bag according to the purpose.

When the blood cell separation material is packed into the container, the blood cell separation material may be compressed or may not be compressed. Whether the blood cell separation material is compressed may be determined appropriately based on the material and the like of the blood cell separation material. One preferred example of the usage form of the blood cell separation material is obtained by cutting the blood cell separation material made of a nonwoven fabric into pieces of an appropriate size, and forming a single layer, or a laminate of layers, of the blood cell separation material which has a thickness of about 1 mm to 200 mm. In terms of the fraction separation efficiencies, the thickness is more preferably 1.5 mm to 150 mm, and further more preferably 2 mm to 100 mm. Preferably, the thickness of the single layer or the laminate of layers of the separation material packed in the container is approximately 1 mm to 50 mm. In terms of the fraction separation efficiencies, the thickness is more preferably 1.5 mm to 40 mm, and further more preferably 2 mm to 35 mm.

The blood cell separation material may be rolled up into a rolled-up form and then packed into the container. In the case that the blood cell separation material is used in a rolled-up form, the biological fluid may be allowed to pass through this roll from the inside to the outside or conversely from the outside to the inside for separation of blood cells.

The shape, size, and material of the container for packing the blood cell separation material therein are not particularly limited. The shape of the container may be any shape such as spherical, container-shaped, cassette-shaped, bag-shaped, tubular, or columnar. Specific preferred examples of the container include, but are not limited to, a translucent tubular container having a volume of about 0. 1 mL to 400 mL and a diameter of about 0.1 cm to 15 cm; and a quadratic prism-shaped container having a thickness of about 0.1 cm to 5 cm and having rectangular or square faces with sides having a length of about 0.1 cm to 20 cm.

The container may be made of any structural material. Specific examples of such structural materials include non-reactive polymers, biocompatible metals and alloys, and glasses. Examples of nonreactive polymers include acrylonitrile polymers (e.g. acrylonitrile butadiene styrene terpolymer), halogenated polymers (e.g. polytetrafluoroethylene, polychlorotrifluoroethylene, tetrafluoroethylene-hexafluoropropylene copolymer, polyvinyl chloride), polyamide, polyimide, polysulfone, polycarbonate, polyethylene, polypropylene, polyvinyl chloride-acrylic copolymer, polycarbonate acrylonitrile butadiene styrene, polystyrene, and polymethylpentene. Examples of usable metal materials for the container (biocompatible metals and alloys) include stainless steel, titanium, platinum, tantalum, gold, and alloys of these, gold plated ferroalloy, platinum plated ferroalloy, cobalt chromium alloy, and titanium nitride-coated stainless steel.

Materials having sterilization resistance are particularly preferred and specific examples thereof include polypropylene, polyvinyl chloride, polyethylene, polyimide, polycarbonate, polysulfone, and polymethylpentene.

EXAMPLES

The following examples are offered by way of detailed illustration of the present invention and the present invention is not limited to these examples.

Example 1

A laminate of 28 layers of a polypropylene nonwoven fabric (fiber diameter: 3.5 µm, density K: $8.3 \times 10^4$ g/m$^3$). was packed into a container having a thickness of 6 mm and a diameter of 18 mm, and physiological saline (45 mL) was first passed through the container from an inlet by pressing a syringe by hand. Next, citrate-anticoagulated fresh bovine blood (10 mL) was introduced at 2.5 mL/min and passed through the container, and then physiological saline (10 mL) was passed through the container in the same direction. Subsequently, MEM supplemented with 10% FBS (30 mL) was passed through the container in the direction opposite to the above flow direction by pressing a syringe by hand, and recovered. The blood sample before the above processes, an obtained red blood cell-rich fraction, and an obtained white blood cell-rich fraction were evaluated for blood count using a blood cell counter (K-4500 produced by Sysmex Corp.), and the blood cell recovery rates of the fractions were calculated. Portions of the blood sample before the processes and the recovered separation solution were hemolyzed with FACS Lysing Solution and evaluated for mononuclear cell positivity and granular leukocyte positivity using a flow cytometer (FACSCanto produced by Nippon Becton Dickinson Company, Ltd.). The total numbers of mononuclear cells and granular leukocytes were calculated by multiplying the number of white blood cells by the respective positivities. The mononuclear cell recovery rate and the granular leukocyte recovery rate were determined as percentages calculated by dividing the total numbers of mononuclear cells and granular leukocytes in the recovered separation solution by the total numbers of mononuclear cells and granular leukocytes before the above processes, respectively. Table 1 shows the results.

Example 2

The same procedures as in Example 1 were carried out, except that a laminate of 28 layers of a polybutylene terephthalate nonwoven fabric (fiber diameter: 2.5 µm, density K: $1.0 \times 10^5$ g/m$^3$) was packed. Table 1 shows the results.

Example 3

The same procedures as in Example 1 were carried out, except that a laminate of 28 layers of a polybutylene terephthalate nonwoven fabric (fiber diameter: 3.8 µm, density K: $1.2 \times 10^5$ g/m$^3$) was packed. Table 1 shows the results.

Example 4

The same procedures as in Example 1 were carried out, except that a laminate of 44 layers of a polyethylene terephthalate nonwoven fabric (fiber diameter: 4.1 µm, density K: $1.9 \times 10^5$ g/m$^3$) was packed. Table 1 shows the results.

Example 5

The same procedures as in Example 1 were carried out, except that a laminate of 44 layers of an acrylic nonwoven fabric (fiber diameter: 4.7 µm, density K: $1.4 \times 10^5$ g/m$^3$) was packed. Table 1 shows the results.

Example 6

The same procedures as in Example 1 were carried out, except that a laminate of 22 layers of a nonwoven fabric made of polyethylene terephthalate-polypropylene split fibers (fiber diameter: 10 µm, density K: $1.6 \times 10^5$ g/m$^3$) was packed. Table 1 shows the results.

Example 7

The same procedures as in Example 1 were carried out, except that a laminate of 22 layers of a nonwoven fabric made of polyethylene terephthalate-nylon split fibers (fiber diameter: 10 µm, density K: $1.4 \times 10^5$ g/m$^3$) was packed, and that ACD-anticoagulated fresh bovine blood (10 mL) was used instead of the citrate-anticoagulated fresh bovine blood (10 mL). Table 1 shows the results.

Example 8

The same procedures as in Example 1 were carried out, except that a laminate of 33 layers of a nylon nonwoven fabric (fiber diameter: 5.0 µm, density K: $1.3 \times 10^5$ g/m$^3$) was packed, and that CPD-anticoagulated fresh human blood (10 mL) was used instead of the citrate-anticoagulated fresh bovine blood (10 mL). Table 1 shows the results.

Example 9

The same procedures as in Example 8 were carried out, except that a laminate of 30 layers of a polypropylene nonwoven fabric (fiber diameter: 2.4 µm, density K: $5.6 \times 10^4$ g/m$^3$) was packed. Table 1 shows the results.

Example 10

The same procedures as in Example 8 were carried out, except that a laminate of 28 layers of a polypropylene nonwoven fabric (fiber diameter: 3.5 µm, density K: $8.3 \times 10^4$ g/m$^3$) was packed. Table 1 shows the results.

Example 11

The same procedures as in Example 8 were carried out, except that a laminate of 28 layers of a polypropylene nonwoven fabric (fiber diameter: 5.7 µm, density K: $1.2 \times 10^5$ g/m$^3$) was packed. Table 1 shows the results.

Example 12

The same procedures as in Example 8 were carried out, except that a laminate of 84 layers of a polybutylene terephthalate nonwoven fabric (fiber diameter: 1.8 µm, density K: $9.1 \times 10^4$ g/m$^3$) was packed. Table 1 shows the results.

Example 13

The same procedures as in Example 8 were carried out, except that a laminate of 28 layers of a polybutylene terephthalate nonwoven fabric (fiber diameter: 2.5 µm, density K: $1.0 \times 10^5$ g/m$^3$) was packed. Table 1 shows the results.

Example 14

The same procedures as in Example 8 were carried out, except that a laminate of 28 layers of a polybutylene terephthalate nonwoven fabric (fiber diameter: 3.8 µm, density K: $1.2 \times 10^5$ g/m$^3$) was packed. Table 1 shows the results.

Example 15

The same procedures as in Example 8 were carried out, except that a laminate of 28 layers of a polybutylene terephthalate nonwoven fabric (fiber diameter: 5.3 µm, density K: $1.1 \times 10^5$ g/m$^3$) was packed. Table 1 shows the results.

Example 16

The same procedures as in Example 13 were carried out, except that CPD-anticoagulated swine umbilical cord blood was used instead of the CPD-anticoagulated fresh human blood (10 mL). Table 1 shows the results.

Example 17

The same procedures as in Example 13 were carried out, except that a 10% dextran injection was used instead of the MEM supplemented with 10% FBS. Table 1 shows the results.

Example 18

The same procedures as in Example 7 were carried out, except that citrate-anticoagulated bovine blood was used instead of the ACD-anticoagulated human blood, and that physiological saline was used instead of the MEM supplemented with 10% FBS. Table 1 shows the results.

Example 19

The same procedures as in Example 3 were carried out, except that CPD-anticoagulated swine bone marrow (10 mL) was used instead of the citrate-anticoagulated fresh bovine blood (10 mL). Table 1 shows the results.

Comparative Example 1

The same procedures as in Example 8 were carried out, except that a laminate of 40 layers of a polybutylene terephthalate nonwoven fabric (fiber diameter: 16 μm, density K: $5.1 \times 10^4$ g/m$^3$) was packed. Table 1 shows the results.

Comparative Example 2

The same procedures as in Example 1 were carried out, except that a laminate of 36 layers of a glass-polyethylene terephthalate nonwoven fabric (fiber diameters: less than 0.59 μm, and 9.3 μm; density K: $2.0 \times 10^5$ g/m$^3$) was packed. Table 1 shows the results.

Comparative Example 3

The same procedures as in Example 1 were carried out, except that a laminate of 24 layers of a glass-polyethylene terephthalate nonwoven fabric (fiber diameters: less than 0.84 μm, and 8.4 μm; density K: $2.2 \times 10^5$ g/m$^3$) was packed. Table 1 shows the results.

Comparative Example 4

The same procedures as in Example 1 were carried out, except that a laminate of 56 layers of a vinylon nonwoven fabric (fiber diameter: 30 μm, density K: $3.2 \times 10^5$ g/m$^3$) was packed. Table 1 shows the results.

Comparative Example 5

The same procedures as in Example 1 were carried out, except that a laminate of 6 layers of an acrylic-polyethylene terephthalate nonwoven fabric (fiber diameter: 22 μm, density K: $2.1 \times 10^5$ g/m$^3$) was packed. Table 1 shows the results.

TABLE 1

| | | Nonwoven fabric | | | | Red blood cell-rich fraction | | |
| --- | --- | --- | --- | --- | --- | --- | --- | --- |
| | Biological fluid | Material | Fiber diameter [μm] | Density K [g/m$^3$] | Separation solution | Red blood cell recovery rate [%] | White blood cell recovery rate [%] | Platelet recovery rate [%] |
| Example 1 | Citrate-anticoagulated bovine blood | PP | 3.5 | $8.3 \times 10^4$ | Medium supplemented with FBS | 97 | 0 | 46 |
| Example 2 | Citrate-anticoagulated bovine blood | PBT | 2.5 | $1.0 \times 10^5$ | Medium supplemented with FBS | 99 | 0 | 36 |
| Example 3 | Citrate-anticoagulated bovine blood | PBT | 3.8 | $1.2 \times 10^5$ | Medium supplemented with FBS | 96 | 0 | 44 |
| Example 4 | Citrate-anticoagulated bovine blood | PET | 4.1 | $1.9 \times 10^5$ | Medium supplemented with FBS | 98 | 16 | 36 |
| Example 5 | Citrate-anticoagulated bovine blood | Acrylic | 4.7 | $1.4 \times 10^5$ | Medium supplemented with FBS | 96 | 4 | 55 |
| Example 6 | Citrate-anticoagulated bovine blood | PET-PP split fiber | 10 | $1.6 \times 10^5$ | Medium supplemented with FBS | 99 | 16 | 52 |
| Example 7 | ACD-anticoagulated human blood | PET-nylon split fiber | 10 | $1.4 \times 10^5$ | Medium supplemented with FBS | 100 | 0 | 2 |
| Example 8 | CPD-anticoagulated human blood | Nylon | 5.0 | $1.3 \times 10^5$ | Medium supplemented with FBS | 94 | 8 | 0 |
| Example 9 | CPD-anticoagulated human blood | PP | 2.4 | $5.6 \times 10^4$ | Medium supplemented with FBS | 96 | 4 | 0 |
| Example 10 | CPD-anticoagulated human blood | PP | 3.5 | $8.3 \times 10^4$ | Medium supplemented with FBS | 98 | 8 | 0 |
| Example 11 | CPD-anticoagulated human blood | PP | 5.7 | $1.2 \times 10^5$ | Medium supplemented with FBS | 96 | 38 | 2 |
| Example 12 | CPD-anticoagulated human blood | PBT | 1.8 | $9.1 \times 10^4$ | Medium supplemented with FBS | 97 | 4 | 0 |
| Example 13 | CPD-anticoagulated human blood | PBT | 2.5 | $1.0 \times 10^5$ | Medium supplemented with FBS | 97 | 4 | 0 |
| Example 14 | CPD-anticoagulated human blood | PBT | 3.8 | $1.2 \times 10^5$ | Medium supplemented with FBS | 100 | 4 | 4 |
| Example 15 | CPD-anticoagulated human blood | PBT | 5.3 | $1.1 \times 10^5$ | Medium supplemented with FBS | 98 | 25 | 9 |
| Example 16 | CPD-anticoagulated swine umbilical cord blood | PBT | 2.5 | $1.0 \times 10^5$ | Medium supplemented with FBS | 98 | 0 | 17 |
| Example 17 | CPD-anticoagulated human blood | PBT | 2.5 | $1.0 \times 10^5$ | 10% dextran | 98 | 4 | 0 |

TABLE 1-continued

| | | | | | | | | |
|---|---|---|---|---|---|---|---|---|
| Example 18 | Citrate-anticoagulated bovine blood | PET-nylon split fiber | 10 | 1.4 × 10⁵ | Physiological saline | 98 | 8 | 46 |
| Example 19 | CPD-anticoagulated swine bone marrow | PBT | 3.8 | 1.2 × 10⁵ | Medium supplemented with FBS | 100 | 10 | 23 |
| Comparative Example 1 | CPD-anticoagulated human blood | PBT | 16 | 5.1 × 10⁴ | Medium supplemented with FBS | 100 | 86 | 27 |
| Comparative Example 2 | Citrate-anticoagulated bovine blood | Glass-PET | 0.59/9.3 | 2.0 × 10⁵ | Medium supplemented with FBS | 97 | 0 | 40 |
| Comparative Example 3 | Citrate-anticoagulated bovine blood | Glass-PET | 0.84/8.4 | 2.2 × 10⁵ | Medium supplemented with FBS | 97 | 0 | 14 |
| Comparative Example 4 | Citrate-anticoagulated bovine blood | Vinylon | 30 | 3.2 × 10⁵ | Medium supplemented with FBS | 96 | 72 | 89 |
| Comparative Example 5 | Citrate-anticoagulated bovine blood | Acrylic-PET | 22 | 2.1 × 10⁵ | Medium supplemented with FBS | 99 | 108 | 86 |

| | White blood cell-rich fraction | | | | |
|---|---|---|---|---|---|
| | Red blood cell recovery rate [%] | Platelet recovery rate [%] | Mononuclear cell recovery rate (A) [%] | Granular leukocyte recovery rate (B) [%] | A/B |
| Example 1 | 1 | 17 | 100 | 59 | 1.7 |
| Example 2 | 1 | 11 | 100 | 29 | 3.4 |
| Example 3 | 1 | 17 | 100 | 39 | 2.6 |
| Example 4 | 2 | 27 | 97 | 49 | 2.0 |
| Example 5 | 2 | 13 | 98 | 47 | 2.1 |
| Example 6 | 1 | 19 | 81 | 40 | 2.0 |
| Example 7 | 0 | 4 | 70 | 47 | 1.5 |
| Example 8 | 5 | 0 | 83 | 32 | 2.6 |
| Example 9 | 2 | 21 | 100 | 6 | 16.7 |
| Example 10 | 3 | 28 | 100 | 13 | 7.7 |
| Example 11 | 1 | 34 | 83 | 32 | 2.6 |
| Example 12 | 1 | 32 | 95 | 15 | 6.3 |
| Example 13 | 2 | 28 | 100 | 28 | 3.6 |
| Example 14 | 1 | 32 | 100 | 44 | 2.3 |
| Example 15 | 2 | 36 | 94 | 45 | 2.1 |
| Example 16 | 3 | 20 | 85 | 49 | 1.7 |
| Example 17 | 1 | 47 | 93 | 21 | 4.4 |
| Example 18 | 2 | 7 | 57 | 80 | 0.7 |
| Example 19 | 1 | 44 | 81 | 48 | 1.7 |
| Comparative Example 1 | 1 | 15 | 11 | 11 | 1.0 |
| Comparative Example 2 | 1 | 8 | 42 | 39 | 1.1 |
| Comparative Example 3 | 2 | 11 | 36 | 32 | 1.2 |
| Comparative Example 4 | 0 | 0 | 25 | 23 | 1.1 |
| Comparative Example 5 | 0 | 0 | 0 | 0 | — |

Example 20

The MEM supplemented with 10% FBS, the 10% dextran injection, and the physiological saline were evaluated for viscosity at 25° C. Their viscosities were 2.9 mPa·s, 5.3 mPa·s, and 1.1 mPa·s, respectively.

Figure 1:
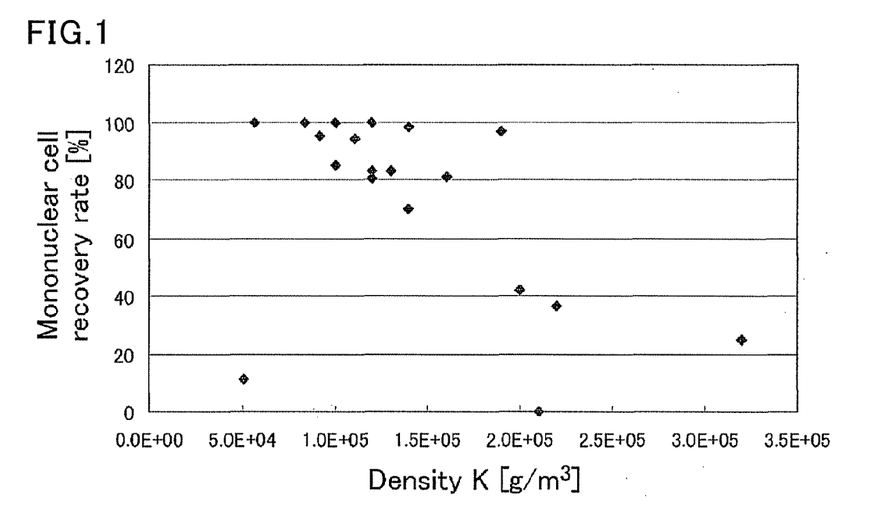
FIG. 1 is a graph illustrating the relationship between densities K and mononuclear cell recovery rates.

FIG. 1 is a graph illustrating the relationship between the densities K of the nonwoven fabrics and the mononuclear cell recovery rates. The densities K were determined by dividing the basis weights by the thicknesses. The thicknesses were measured using a dial thickness gauge (gauge head diameter: 25 mm, pressure: 0.7 kPa). The basis weights were determined by measuring the weights of 10 cm-square samples cut out from the nonwoven fabrics.

Figure 2:
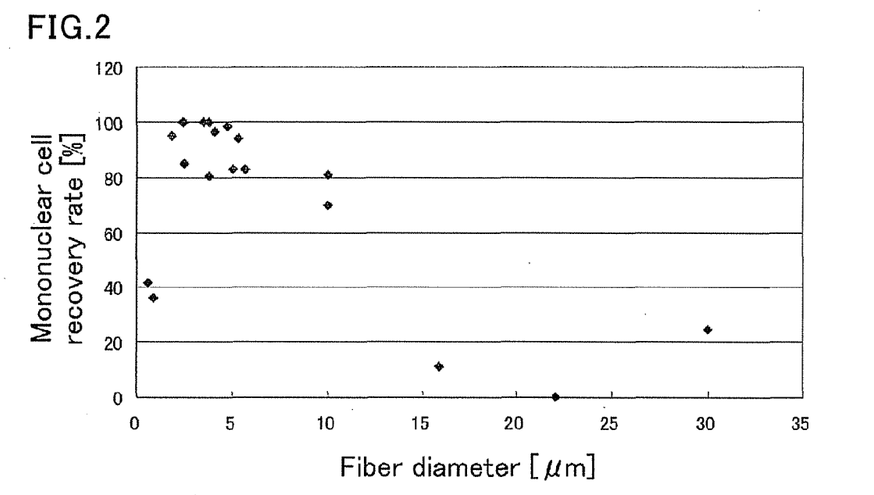
FIG. 2 is a graph illustrating the relationship between fiber diameters and mononuclear cell recovery rates.

FIG. 2 is a graph illustrating the relationship between the fiber diameters of the nonwoven fabrics and the mononuclear cell recovery rates. The fiber diameters were determined as follows: photographing each nonwoven fabric by a scanning electron microscope; measuring the diameters of 100 fibers based on a scale on the photograph; and averaging the diameters.

The results shown above clearly demonstrate that the use of the separation material and the separation method described herein makes it possible to easily and rapidly separate a red blood cell-rich fraction, a white blood cell-rich fraction, and/or a platelet-rich fraction from a biological fluid without the necessity of performing centrifugation. It is also clearly demonstrated that the use of a nonwoven fabric having a density K of $2.0 \times 10^4$ to $1.9 \times 10^5$ and a fiber diameter of 1 μm to 15 μm gives a mononuclear cell-rich fraction. The comparative examples demonstrate that the use of a nonwoven fabric having a density K outside the above range or a nonwoven fabric including a fiber with a fiber diameter smaller or larger than the above range reduces the separation efficiencies.

EXPLANATION OF SYMBOLS

1 Chamber
2 Container packed with blood cell separation material
3 Biological fluid bag
4 Washing solution bag (also serving as priming solution bag)
5 Red blood cell-rich fraction recovery bag
6 White blood cell-rich fraction recovery bag (mononuclear cell-rich fraction recovery bag)

7 Recovery port
8, 9, 10 Three-way stopcock
11-17 Line

The invention claimed is:

1. A method for separating blood cell components from a biological fluid, comprising:
   (a) capturing white blood cells and platelets on a blood cell separation material by contacting the biological fluid with the blood cell separation material, thereby providing a red blood cell-rich fraction; and
   (b) separating a white blood cell-rich fraction from the resulting blood cell separation material using a separation solution,
   wherein the blood cell separation material comprises a nonwoven fabric,
   wherein the nonwoven fabric comprises a polyethylene terephthalate fiber or a polybutylene terephthalate fiber,
   wherein the nonwoven fabric has a density K of $2.0 \times 10^4$ to $1.9 \times 10^5$ and has a fiber diameter of 1μm to 15μm, and the white blood cell-rich fraction is a mononuclear cell-rich fraction, and
   wherein a ratio of a mononuclear cell recovery rate to a granular leukocyte recovery rate of the white blood-cell rich fraction or the mononuclear cell-rich fraction is larger than 1.0.

2. The separation method according to claim 1, wherein the blood cell separation material is packed in a container having an inlet and an outlet for the biological fluid, and the contact of the biological fluid with the blood cell separation material is accomplished by introducing the biological fluid from the inlet.

3. The separation method according to claim 1, wherein in the step (a), after the contact of the biological fluid with the blood cell separation material, remaining red blood cells are washed out of the resulting blood cell separation material with a washing solution.

4. The separation method according to claim 2, wherein in the step (b), the separation solution is introduced from the outlet for the biological fluid to separate and recover white blood cells.

5. The separation method according to claim 1, wherein the separation solution comprises physiological saline, a buffer, dextran, a culture medium, or an infusion.

6. The separation method according to claim 1, wherein the biological fluid is blood, bone marrow, umbilical cord blood, menstrual blood, or a tissue extract.

7. The separation method according to claim 1, wherein before the contact of the blood cell separation material with the biological fluid in the step (a), the blood cell separation material is preliminarily contacted with a solution.

8. The separation method according to claim 7, wherein the solution for preliminarily contacting the blood cell separation material comprises physiological saline or a buffer.

9. The separation method according to claim 8, wherein the nonwoven fabric further comprises a polyester fiber, a polypropylene fiber, a nylon fiber, or an acrylic fiber.

10. The separation method according to claim 9, wherein the nonwoven fabric further comprises a nylon fiber, or a polypropylene fiber.

11. The separation method according to claim 1, wherein the nonwoven fabric comprises a split fiber.

12. The separation method according to claim 1, wherein the separation solution is a solution having a viscosity of from 1 mPa·s or higher to lower than 5 mPa·s.

13. The separation method according to claim 1, wherein a platelet recovery rate of the white blood cell-rich fraction or the mononuclear cell-rich fraction is not more than a white blood cell recovery rate of the white blood cell-rich fraction or the mononuclear cell-rich fraction.

14. The separation method according to claim 1, wherein a platelet recovery rate of the white blood cell-rich fraction or the mononuclear cell-rich fraction is not more than a mononuclear cell recovery rate of the white blood cell-rich fraction or the mononuclear cell-rich fraction.

15. The separation method according to claim 1, wherein the white blood cell-rich fraction or the mononuclear cell-rich fraction comprises a hematopoietic stem cell, a mesenchymal stem cell, or a CD34-positive cell.

* * * * *